(12) United States Patent
Groux et al.

(10) Patent No.: US 8,703,431 B2
(45) Date of Patent: Apr. 22, 2014

(54) POLYPEPTIDES FOR THE IN VITRO ASSESSMENT OF THE SENSITISING POTENTIAL OF A TEST COMPOUND

(75) Inventors: Hervé Groux, Le Rouret (FR); Jean-Marc Sabatier, Rousset (FR)

(73) Assignee: Immunosearch, Le Plan de Grasse (FR)

( * ) Notice: Subject to any disclaimer, the term of this patent is extended or adjusted under 35 U.S.C. 154(b) by 34 days.

(21) Appl. No.: 13/318,064

(22) PCT Filed: Apr. 30, 2010

(86) PCT No.: PCT/EP2010/055895
§ 371 (c)(1),
(2), (4) Date: Jan. 9, 2012

(87) PCT Pub. No.: WO2010/125176
PCT Pub. Date: Nov. 4, 2010

(65) Prior Publication Data
US 2012/0149130 A1    Jun. 14, 2012

(30) Foreign Application Priority Data
Apr. 30, 2009  (FR) .................. 09 52929

(51) Int. Cl.
*G01N 33/53* (2006.01)
*C07K 14/00* (2006.01)

(52) U.S. Cl.
USPC .................. 435/7.1; 530/350; 530/300

(58) Field of Classification Search
None
See application file for complete search history.

(56) References Cited

U.S. PATENT DOCUMENTS 7,074,559 B2 *  7/2006  Kapur et al. .................. 435/6.15

FOREIGN PATENT DOCUMENTS

| EP | 1 574 569 A1 | 9/2005 |
|---|---|---|
| WO | WO 01/90150 | * 11/2001 |
| WO | WO 2009/052390 A1 | 4/2009 |

OTHER PUBLICATIONS

Chothia et al., "The relation between the divergence of sequence and structure in proteins", The EMBO Journal vol. 5 No. 4 pp. 823-826, 1986.*
Aleksic et al., "Reactivity Profiling: Covalent Modification of Single Nucleophile Peptides for Skin Sensitization Risk Assessment", Toxicological Sciences, vol. 108, No. 2 (2009) pp. 401-411.
Gerberick et al., "Development of a Peptide Reactivity Assay for Screening Contact Allergens", Toxicological Sciences, vol. 81 (2004) pp. 332-343.
Gerberick et al., "Quantification of Chemical Peptide Reactivity for Screening Contact Allergens: A Classification Tree Model Approach", Toxicological Sciences, vol. 97, No. 2 (2007) pp. 417-427.
International Search Report issued in PCT/EP2010/055895 on Apr. 30, 2009.
Mutschler et al., "Mechanistic assessment of peptide reactivity assay to predict skin allergens with Kathon CG isothiazolinones", Toxicology in Vitro, vol. 23 (2009) pp. 439-446.
Roberts et al., "High Throughput Kinetic Profiling Approach for Covalent Binding to Peptides: Application to Skin Sensitization Potency of Michael Acceptor Electrophiles", Chem. Res. Toxicol., vol. 22 (2009) pp. 592-603.
Seo et al., "Expression of Neutrophil Gelatinase-Associated Lipocalin in Skin Epidermis", J. of Investigative Dermatology, vol. 126 (2006) pp. 510-512.
Takeda et al., "Lipocalin-type prostaglandin D synthase as a melanocyte marker regulated by MITF", Biochemical and Biophysical Research Communications, vol. 339 (2006) pp. 1098-1106.

* cited by examiner

*Primary Examiner* — Suzanne M Noakes
(74) *Attorney, Agent, or Firm* — Birch, Stewart, Kolasch & Birch, LLP

(57) ABSTRACT

The invention relates to novel polypeptides and to the use thereof for the in vitro assessment of the sensitizing potential of a test compound, to a method for the in vitro assessment of the sensitizing potential of a test compound, to an in vitro method for selecting a compound suitable for reducing the sensitization, as well as to kits for implementing such methods.

13 Claims, No Drawings

POLYPEPTIDES FOR THE IN VITRO ASSESSMENT OF THE SENSITISING POTENTIAL OF A TEST COMPOUND

The present invention relates to novel polypeptides and to the use thereof for the in vitro assessment of the sensitising potential of a test compound, to a method for the in vitro assessment of the sensiting potential of a test compound, to an in vitro assessment method for selecting a compound able to reduce sensitisation, and to kits for implementing such methods.

The perfumery and cosmetics industries must remain competitive and efficient and continue to regularly propose new products, with the constraint of meeting the safety standards for humans and their environment relating to use thereof. However, contact allergy is one of the major risks associated with the use of a perfume or a cosmetic product.

Cutaneous contact allergy (or atopic dermatitis) is a major public health problem in humans. It represents a serious constraining environmental immunotoxic manifestation, the effects of which are important to anticipate when products liable to cause them are put on the market. Skin sensitisation and consequently the associated allergic manifestation is the result first of the interaction of an allergenic molecule with specialised cells of the epidermis, the antigen-presenting cells (Langerhans cells, dendritic cells) and then secondly the presentations thereof by these cells with T $CD4^+$ and $CD8^+$ effecting lymphocytes. It is the latter that are at the basis of the allergenic and inflammatory reaction. Nevertheless, allergens, in particular those that may be present in a perfume or cosmetic product, are small molecules that may not be recognised directly. Recognition thereof requires their prior association with self-proteins. Thus it is the heterodimer complex neoformed in the skin that will subsequently be presented to the T cells in the proximal ganglions. Consequently the ability of a chemical molecule (composed of perfume or a cosmetic ingredient) to associate with a protein of the user of this perfume is an obligatory precursor to the inducing of a consequent pathological reaction.

Until now, animals were used to identify the sensitising molecules at the skin level and the LLNA (local lymph node assay) based on the induced proliferation of the ganglion lymphocytes after contact with the sensitiser has been developed. This test has been adopted as "Testing guideline 429" by the Organisation for Economic Cooperation and Development (OECD) and is still considered at the present time to be the reference test for determining a sensitising chemical agent.

The new European constraints now impose the use of methods not using animals and it is therefore essential to develop alternative methods for determining whether a novel perfuming composition is liable to represent a danger for humans through its sensitising properties.

Surprisingly, the inventors showed that sequences of two enzymes in the lipocalin family, present in the skin and having important homologous sequences, permit to screen in vitro compounds liable to behave as allergens. These enzymes are "neutrophil gelatinase associated lipocalin" (NGAL, also referred to as lipocalin 2) (SEO et al, *Expression of neutrophil gelatinase-associated lipocalin in skin epidermis*, J. Invest. Dermatol, 126, 510-412; 2006), and "prostaglandin D synthase" (L-PGDS) (TAKEDA et al, *Lipocalin-type prostaglandin D synthase as a melanocyte marker regulated by MTIF*, BBRC, 339, 1098-1106; 2006).

NGAL was originally identified as a 25 kDa protein associated covalently with "neutrophil gelatinase" of 92 kDa (or gelatinase B, MMP-9). Crystallographic analysis has shown that the natural ligands of this enzyme are a variety of bacterial ferric siderophores thus acting as a bacteriostatic. In the kidney, this enzyme fulfils the same role by delivering iron into the cells of the nephron. NGAL is induced by calcium in keratinocytes in culture and its presence in the human and mouse skin has been confirmed, particularly at the epidermis (in keratinocytes solely) and hair follicles by in situ hybridisation.

L-PGDS, the role of which initially described is to isomerise prostaglandin H2 into prostaglandin D2, also functions as a lipophilic protein of the extracellular spaces, the known ligands of which are bilirubin, retinaldehyde and retinoic acid. Recent studies have shown that L-PGDS is present in the Langerhans cells, melanocytes, mastocytes, histiotcytes and macrophages (but not in keratinocytes) in rats.

The inventors then identified particular sequences of these lipocalins or derivatives thereof, for developing methods for the in vitro assessment of the sensitising potential of compounds liable to behave as allergens.

Thus the present invention relates to an isolated polypeptide comprising a sequence chosen from the sequence SEQ ID NO: 1, 2, 3, 4, 5, 6, 7, 8, 9, 10, 11, 12 and 13 and derivatives of these, preferably to an isolated polypeptide comprising a sequence chosen from the sequence SEQ ID NO: 1, 2, 3 and 4, even more preferentially an isolated polypeptide comprising the sequence SEQ ID NO: 1 or the sequence SEQ ID NO: 3, and even more preferably an isolated polypeptide comprising the sequence SEQ ID NO: 1.

Said sequences are listed below:

```
                                        (SEQ ID NO: 1)
X1ACAX2DELX3EX4

(SEQ ID NO: 2)
X1EX2LEDX3ACAX4

(SEQ ID NO: 3)
ECGX1DELX2EX3

(SEQ ID NO: 4)
X1EX2LEDX3GCE, (SEQ ID NO: 5)
LYGRTX1ELTSELX2ENFIRFSX3SLGLPEN (SEQ ID NO: 6)
LYSRSQNPRAEVX1EHFTTFAX2SLGFTEE (SEQ ID NO: 7)
LYGRTX1ELSPELX2ERFTFAX3SLGLX4

(SEQ ID NO: 8)
LYSRTQTLX1DELX2EX3FTTFSX4AQGLT (SEQ ID NO: 9)
RQNQCETX1

(SEQ ID NO: 10)
TLYGRTX1EL (SEQ ID NO: 11)
X1ERFTRFAX2

(SEQ ID NO: 12)
X1EX2FTTFSX3

(SEQ ID NO: 13)
LYGRTX1ELS
``` where X1, X2, X3 and X4 are independently chosen from lysine, ornithine, diaminobutyrate or diaminoprionate, preferably lysine.

Advantageously, each of the groups X1, X2, X3 and X4 represents a lysine. Thus, advantageously, in the sequence SEQ ID NO: 1, X1, X2, X3 and X4 each represent a lysine group, and thus corresponds to the following sequence SEQ ID NO: 20:

```
                                          (SEQ ID NO: 20)
KACAKDELKEK
```

Preferentially, said sequence SEQ ID NO: 20 has an amine group (NH2) at its C-Terminal end.

Advantageously, in the sequence SEQ ID NO: 2, X1, X2, X3 and X4 each represents a lysine group, and the sequence thus corresponds to the following sequence SEQ ID NO: 21:

```
                                          (SEQ ID NO: 21)
KEKLEDKACAK
```

Advantageously, in the sequence SEQ ID NO: 3, X1, X2 and X3 each represents a lysine group, and the sequence thus corresponds to the following sequence SEQ ID NO: 22:

```
                                          (SEQ ID NO: 22)
ECGKDELKEK
```

Advantageously, in the sequence SEQ ID NO: 4, X1, X2 and X3 each represents a lysine group, and the sequence thus corresponds to the following sequence SEQ ID NO: 23

```
                                          (SEQ ID NO: 23)
KEKLEDKGCE
```

Advantageously, in the sequence SEQ ID NO: 5, X1, X2 and X3 each represents a lysine group, and the sequence thus corresponds to the following sequence SEQ ID NO: 24:

```
                                          (SEQ ID NO: 24)
LYGRTKELTSELKENFIRFSKSLGLPEN
```

Advantageously, in the sequence SEQ ID NO: 6, X1 and X2 each represents a lysine group, and the sequence thus corresponds to the following sequence SEQ ID NO: 25:

```
                                          (SEQ ID NO: 25)
LYSRSQNPRAEVKEHFTTFAKSLGFTEE
```

Advantageously, in the sequence SEQ ID NO: 7, X1, X2, X3 and X4 each represents a lysine group, and the sequence thus corresponds to the following sequence SEQ ID NO: 26:

```
                                          (SEQ ID NO: 26)
LYGRTKELSPELKERFTFAKSLGLK
```

Advantageously, in the sequence SEQ ID NO: 8, X1, X2, X3 and X4 each represents a lysine group, and the sequence thus corresponds to the following sequence SEQ ID NO: 27:

```
                                          (SEQ ID NO: 27)
LYSRTQTLKDELKEKFTTFSKAQGLT
```

Advantageously, in the sequence SEQ ID NO: 9, X1 represents a lysine group, and the sequence thus corresponds to the following sequence SEQ ID NO: 28:

```
                                          (SEQ ID NO: 28)
RQNQCETK
```

Advantageously, in the sequence SEQ ID NO: 10, X1 represents a lysine group, and the sequence thus corresponds to the following sequence SEQ ID NO: 29:

```
                                          (SEQ ID NO: 29)
TLYGRTKEL
```

Advantageously, in the sequence SEQ ID NO: 11, X1 and X2 each represents a lysine group, and the sequence thus corresponds to the following sequence SEQ ID NO: 30:

```
                                          (SEQ ID NO: 30)
KERFTRFAK
```

Advantageously, in the sequence SEQ ID NO: 12, X1, X2 and X3 each represents a lysine group, and the sequence thus corresponds to the following sequence SEQ ID NO: 31:

```
                                          (SEQ ID NO: 31)
KEKFTTFSK
```

Advantageously, in the sequence SEQ ID NO: 13, X1 represents a lysine group, and the sequence thus corresponds to the following sequence SEQ ID NO: 32:

```
                                          (SEQ ID NO: 32)
LYGRTKELS
```

Advantageously, the sequences SEQ ID NO: 1, 2, 3, 4, 5, 6, 7, 8, 9, 10, 11, 12 and 13 may have an acetyl group at their N-terminal end.

Advantageously, the sequences SEQ ID NO: 1, 2, 3, 4, 5, 6, 7, 8, 9, 10, 11, 12 and 13 may have an amine group (NH2) or amide group (CONH2) at their C-terminal end. Preferably, the sequences SEQ ID NO: 1 and SEQ ID NO: 3 have an amine or amide group at their C-Terminal end.

Said isolated polypeptide according to the present invention may be in L form or D form.

Preferably, the polypeptides according to the present invention have a length less than 100 amino acids, preferably less than 80, even more preferably less than 50, even more preferably less than 40 and most preferably less than 30 amino acids.

By "Derivatives" one should understand a polypeptide having one or more sequence mutations not modifying the activity of said polypeptide, in particular a polypeptide having one or more so-called "conservative" mutations and the mutations not affecting the pKa values of the thiol of the cysteine and/or lysine residue and/or having a percentage of identity of at least 80% with the complete sequence of the sequence SEQ ID NO: 1 to 13, preferably at least 90% and even more preferably at least 95%.

By "Conservative mutation" one should understand a mutation chosen from the substitution of a basic amino acid residue by another basic amino acid residue, an acidic amino acid residue by another acidic amino acid residue, a neutral amino acid residue by another neutral amino acid residue, an aliphatic amino acid residue by another aliphatic or aromatic amino acid residue, an aromatic amino acid residue by another aromatic or aliphatic amino acid residue, an amide amino acid residue by another amide amino acid residue, or an alcohol amino acid residue by another alcohol amino acid residue.

By "Percentage of identity" between amino acid sequences one should understand the percentage of identical amino acids between the two sequences to be compared, obtained with the best alignment of said sequences, this percentage being purely statistical and the differences between the two sequences being randomly distributed in the amino acid sequences. "Best alignment" means the alignment for which the percentage of identity is the highest. The sequence comparison between two amino acid sequences is in general made by comparing these previously-aligned sequences according to the best alignment; this comparison is made on comparison segments in order to identify and compare the similarities of regions. The best alignment of sequences can be made, apart from manually, by the use of the global homology algorithm developed by SMITH and WATERMAN (*Ad. App. Math.*, vol. 2, p. 482, 1981), the local homology algorithm developed by NEDDLEMAN and WUNSCH (J. Mol. Biol., vol. 48, p. 443, 1970), using the method of similarities developed by PEARSON and LIPMAN (Proc. Natl. Acd. Sci. USA, vol. 85, p. 2444, 1988), using software utilising such algorithms (GAP, BESTFIT, BLAST P, BLAST N, FASTA, TFASTA in the "Wisconsin Genetics Software Package", Genetics Computer Group, 575 Science Dr., Madison, Wis., USA), using the MUSCLE multiple alignment algorithms (Edgar, Robert C., Nucleic Acids Research, vol. 32, p. 1792, 2004). In order to obtain the best local alignment, it may be preferable to use the BLAST software, with the BLOSUM 62 matrix or the PAM 30 matrix. The percentage of identity between two amino acid sequences is determined by comparing these two aligned sequences in an optimum fashion, the amino acid sequences being able to comprise additions or deletions with respect to the reference sequence in order to obtain an optimum alignment between the two sequences. The identity percentage is calculated by determining the number of identical positions between the two sequences, and dividing this number by the total number of positions compared, and multiplying this number by one hundred.

According to a preferred embodiment, said isolated polypeptide consists of a sequence chosen from the sequence SEQ ID NO: 1, 2, 3, 4, 5, 6, 7, 8, 9, 10, 11, and 13 and derivatives thereof, preferably a sequence chosen from the sequence SEQ ID NO: 1, SEQ ID NO: 2, SEQ ID NO: 3 and SEQ ID NO: 4, and derivatives thereof, preferably a sequence chosen from the sequence SEQ ID NO: 1 and SEQ ID NO: 3, even more preferably the sequence SEQ ID NO: 1.

The isolated polypeptide consisting of the sequence SEQ ID NO: 1, and even more preferably the sequence SEQ ID NO: 20, is particularly preferred since synthesis and purification thereof are easy, it has excellent solubility and is easy to handle since it is slightly electrostatic, it is only very slightly dimerised, which facilitates use thereof in the methods according to the present invention, and finally it makes it possible to detect the allergens fixed on said sequence in a single reaction step.

According to another aspect, the present invention relates to a nucleotide sequence comprising a nucleic acid sequence coding for a polypeptide as defined above.

The nucleotide sequence according to the present invention can be in RNA or DNA form, preferably in DNA form.

Said DNA can be in double-strand or single-strand form.

According to another aspect, the present invention relates to a method for in vitro assessment of the sensitising potential of a test compound, comprising the steps of:

a) contacting a test compound with an isolated polypeptide comprising a sequence chosen from the sequences SEQ ID NO: 1, 2, 3, 4, 5, 6, 7, 8, 9, 10, 11, 12, 13, 14, 15, 16 and 17 and derivatives thereof;

b) measuring any biding of said compound with said polypeptide.

Naturally the assessment method can also be carried out ex vivo.

The sequence SEQ ID NO: 14 represents the polypeptide sequence of human lipocalin 2:

```
                                        (SEQ ID NO: 14)
MPLGLLWLGLALLGALHAQAQDSTSDLIPAPPLSKVPLQQNFQDNQFQGK

WYVVGLAGNAILREDKDPQKMYATIYELKEDKSYNVTSVLFRKKKCDYWI

RTFVPGCQPGEFTLGNIKSYPGLTSYLVRVVSTNYNQHAMVFFKKVSQNR

EYFKITLYGRTKELTSELKENFIRFSKYLGLPENHIVFPVPIDQCIDG
```

The sequence SEQ ID NO: 15 represents the polypeptide sequence of mouse lipocalin 2:

```
                                        (SEQ ID NO: 15)
MALSVMCLGLALLGVLQSQAQDSTQNLIPAPSLLTVPLQPDFRSDQFRGR

WYVVGLAGNAVQKKTEGSFTMYSTIYELQENNSYNVTSILVRDQDQGCRY

WIRTFVPSSRAGQFTLGNMHRYPQVQSYNVQVATTDYNQFAMVFFRKTSE

NKQYFKITLYGRTKELSPELKERFTRFAKSLGLKDDNIIFSVPTDQCIDN
```

The sequence SEQ ID NO: 16 represents the polypeptide sequence of human prostaglandin D synthase:

```
                                        (SEQ ID NO: 16)
MATHHTLWMGLALLGVLGDLQAAPEAQVSVQPNFQQDKFLGRWFSAGLAS

NSSWLREKKAALSMCKSVVAPATDGGLNLTSTFLRKNQCETRTMLLQPAG

SLGSYSYRSPHWGSTYSVSVVETDYDQYALLYSQGSKGPGEDFRMATLYS

RTQTPRAELKEKFTAFCKAQGFTEDTIVFLPQTDKCMTEQ
```

The sequence SEQ ID NO: 17 represents the polypeptide sequence of mouse prostaglandin D synthase:

```
                                        (SEQ ID NO: 17)
MAALRMLWMGLVLLGLLGFPQTPAQGHDTVQPNFQQDKFLGRWYSAGLAS

NSSWFREKKAVLYMCKTVVAPSTEGGLNLTSTFLRKNQCETKIMVLQPAG

APGHYTYSSPHSGSIHSVSVVEANYDEYALLFSRGTKGPGQDFRMATLYS

RTQTLKDELKEKFTTFSKAQGLTEEDIVFLPQPDKCIQE
```

Advantageously, one or more of the lysine residues of the sequences SEQ ID NO: 14, SEQ ID NO: 15, SEQ ID NO: 16 and SEQ ID NO: 17 and can be replaced by ornithine, diaminobutyrate or diaminopropionate.

Preferably, the isolated polypeptide comprises a sequence chosen from the sequences SEQ ID NO: 1, 2, 3, 4, 5, 6, 7, 8, 9, 10, 11, 12 and 13 and derivates thereof.

The measurement of any bond obtained at step b) can optionally be compared with a negative control carried out in the absence of the test compound or in the presence of a compound known to be non-sensitising, such as for example chlorobenzene (Cbz) or lactic acid (LA), or a positive control carried out with a known ligand of said polypeptide.

Thus said method according to the present invention can also comprise a step c) of determining the sensitising potential of a test compound. The higher the percentage of binding, the greater will be the sensitising potential.

Said binding may for example be a covalent, hydrogen, saline, electrostatic or Van der Waals binding, a radical attack, etc. Said bond is preferably a covalent bond.

The measurement of the binding can be carried out by any technique of measuring a binding well known to persons skilled in the art. By way of example, the measurement of a binding by means of marking, which may be of the antigen, fluorescent, enzymatic or radioactive type, separation by liquid chromatography (HPLC), use of the surface plasmon resonance technique, etc. can be cited.

In a preferred embodiment, the polypeptide is bound to an antigen marker and the measurement of the bonding of said test compound with said polypeptide is carried out by means of a detectable antibody and directed against said antigen marker.

This antigen marker may be any type of marker known to persons skilled in the art and may in particular be chosen from a sequence of polyhistidine amino acids (polyHis), a cMyc element, Flag or an isolated sequence of haemagglutinin or V5 protein. The polyHis sequence preferably contains 4 to 6 histidine residues. Preferentially, the antigen marker is a sequence of polyhistidine amino acids (polyHis).

The antibodies used to detect this antigen marker may be polyclonal or monoclonal. They may be produced by conventional techniques known to persons skilled in the art. They may be commercial antibodies. Among these, the conjugate penta-His HRP antibody (QIAGEN), the anti-6x His Abcam 9108 rabbit antibody, the –6x His HRP marked rabbit antibody (raifort peroxidase) Abcam 1187, the -anti-5x His Qiagen 34698 mouse antibody and the -anti-poly-His Sigma H-1029 antibody can be cited.

The antibodies can be coupled to detectable markers, known to persons skilled in the art, such as enzymes (for example horseradish peroxidase HRP), radioactive markers, fluorescent agents, magnetic particles, etc. Preferentially, the antibody is coupled to HRP (HorseRadish Peroxidase).

The immunodetection can be carried out by any suitable technique, for example Western Blot, Dot Blot, etc.

In another preferred embodiment, the polypeptide is bound to a fluorescent marker and the bond of said test compound with said polypeptide is measured by fluorometry. The fluorescent marking may be direct or indirect, the fluorophore being fixed directly to the polypeptide or by means of another marker. The fluorescent marker may for example be fluorescine, RPE (R-Phycoerythrin), GFP (Green Fluorescent Protein), APC (AlloPhycoCyanin), cyanines or Europium.

In another preferred embodiment, the polypeptide is bound to an enzymatic marker and the measurement of the binding of said test compound with said polypeptide is carried out by fluorometry, luminescence or colorimetry, according to the substrate used during the enzymatic reaction.

The measurement of the bonding of said test compound with said polypeptide can in particular be carried out by means of colorimetric substrate (p-Nitrophenyl Phosphate or pNPP), a fluorescent substrate (Fluorescein DiPhosphate or FDP) or luminescent substrate (Lumi-Phos™), the measurement of the interaction then being carried out respectively by spectrophotometry at 405 nm, by fluorimetry (excitation: 485 nm; emission: 535 nm) or by luminescence.

The polypeptide can be fixed to a support. The support preferentially used for implementing the method according to the present invention is a plate, a ball or a chip.

The polypeptides used in the method according to the present invention can be prepared by any technique known to persons skilled in the art, in particular by artificial synthesis and more particularly by solid phase synthesis.

The test compound may be a compound of varied nature, structure and origin, in particular a biological compound, a chemical compound, a synthetic compound, etc.

The test compound may be any product that is in isolated form or in a mixture with other products. The test compound may be defined in terms of structure and/or composition or be defined on a functional level. The test compound may for example be an isolated and structurally defined product, an isolated product with an undefined structure, a mixture of known and characterised products or a composition comprising one or more products. One or more compounds may be tested, in a mixture or separately.

Such compounds may for example be samples of a cosmetic or dermatological product.

The test compound may be of natural or synthetic origin.

The present invention is particularly suited to identifying a large number of compounds. This simple and effective screening can be performed in a very short length of time. The methods described may in particular be partially automated, thus allowing effective simultaneous screening of various and numerous compounds, either in the form of a mixture or in separate form.

Preferentially, the method according to the invention is carried out in HTS (High Throughput Screening) or MTS (Medium Throughput Screening).

Within the meaning of the present invention, "polypeptide" means a sequence comprising at least two amino acids, and the terms "polypeptide", "peptide" and "protein" may be used indifferently.

By "Sensitising potential" one should understand the risk of the test compound causing an immunological reaction when it is contact with a mammal, preferably a human. Thus the sensitising potential may be considered to be the risk of developing an allergy in contact with the test compound.

Preferably said test compound is able to be applied to the skin. Thus the sensitising potential corresponds to the risk of developing a skin allergy.

Preferably, said test compound is able to form part of the composition of a dermatological or cosmetic composition.

Preferably, the method according to the invention makes it possible to assess whether the test compound is liable to cause a contact allergy or atopical dermatitis.

Preferably, the method according to the present invention is performed in a buffer solution having a pH of between 7.3 and 9.3, even more preferably between 7.8 and 8.8, and particularly preferably the buffer solution having a pH of 8.3.

Preferably, the method according to the present invention is performed at a temperature of between 20° C. and 40° C., more preferably between 25° C. and 35° C., even more preferably between 28° C. and 32° C., and most preferably at 30° C.

Preferably, the method according to the present invention is carried out in darkness.

Preferably, the concentration of polypeptide used for implementing the method according to the present invention is between 0.2 and 1.5 mM, even more preferably between 0.4 and 1.2 mM, even more preferably 1 mM.

Preferably, the concentration of test compound for implementing the method according to the present invention is between 1 and 10 mM, even more preferably between 3 and 7 mM, even more preferably between 4 and 6 mM and most preferably 5 mM.

In a particular embodiment according to the present invention, the test compound may contact with several isolated polypeptides having different sequences.

In a particular embodiment, the assessment method according to the present invention may be a competition test, in which the test compound competes with a compound identified as sensitising. Said compound identified as sensitising may be contact with said isolated polypeptide prior to step a), or simultaneously with step a). Such an embodiment makes it possible to compare the sensitising potential of a test compound with that of a compound identified as sensitising.

According to another aspect, the present invention relates to an in vitro method for selecting a compound able to decrease sensitisation, comprising the steps of:

a) contacting a compound identified as sensitising, an isolated polypeptide comprising a sequence chosen from the sequences SEQ ID NO: 1, 2, 3, 4, 5, 6, 7, 8, 9, 10, 11, 12, 13, 14, 15, 16 and 17 and derivatives thereof, and a candidate compound for reducing sensitisation;

b) measuring any binding of the compound identified as sensitising with said polypeptide.

Said method for selecting a compound able to decrease sensitisation may be carried out under the same conditions as those described previously for the in vitro assessment of the sensitising potential of a test compound.

By "Compound able to decrease sensitisation" one should understand a compound capable of reducing the sensitising potential of a compound identified as sensitising. In other words, by "compound able to decrease sensitisation" one should understand a compound decreasing the risk of causing an immunological reaction in the presence of a compound identified as sensitising. The term "desensitising compound" can also be used to define the "compound able to decrease sensitisation".

Preferably, it will be concluded that a compound is able to decrease sensitisation if it makes it possible to reduce the sensitising potential of a compound identified as sensitising by at least 10%, preferable at least 20%, 30%, 40%, 50%, 60%, 70%, 80%, 90% and preferably 100% with respect to the sensitising potential observed in the absence of said desensitising compound.

By "Compound identified as sensitising" one should understand in particular a compound able to be identified by the method of the present invention, that is to say, in other words, a compound identified as having an allergenic potential.

The compound able to be identified by the method according to the invention may be a compound of varied nature, structure and origin, in particular a biological compound, a chemical, synthetic etc compound.

Preferably, the compound identified as sensitising is chosen from diphenylcyclopropenone (DPCP), lauryl gallate (LG), 3-3-dimethylaminopropylamine (3-DMAPA), cinnamic aldehyde (CA), citral (Cal), 1,4-hydroquinone (HQ), glutaraldehyde (GA), 1,2-benzisothiazolin-3-one (Ben), phenylacetaldehyde (PA) and lilial (Li), preferentially from diphenylcyclopropenone, lauryl gallate, 1,4-hydroquinone and glutaraldehyde, and particular preferably is diphenylcyclopropenone.

Diphenylcyclopropenone is an extremely strong sensitiser; lauryl gallate, 1,4-hydroquinone and glutaraldehyde are strong sensitisers; 3-3-dimethylaminopropylamine, cinnamic aldehyde, citral, 1,2-benzisothiazolin-3-one and phenylacetaldehyde are moderate sensitisers and lilial is a weak sensitiser.

The candidate compound for decreasing sensitisation may be any product that is in isolated form or in a mixture with other products. The candidate compound for decreasing sensitisation may be defined in terms of structure and/or composition or be defined on the functional level. The candidate compound for decreasing sensitisation may for example be an isolated and structurally defined product, an isolated product of undefined structure, a mixture of known characterised products or a composition comprising one or several products. One or several compounds may thus be tested, in a mixture or separately.

The test compound may be of natural or synthetic origin.

The ability of a candidate compound to decrease or inhibit the binding may be assessed by comparing the bonding capacity of a polypeptide comprising at least one sequence chosen from the sequences SEQ ID NO: 1, 2, 3, 4, 5, 6, 7, 8, 9, 10, 11, 12, 13, 14, 15, 16 and 17 and derivatives thereof, with a compound identified as sensitising in the presence of said candidate compound, with the bonding capacity of said polypeptide with said compound identified as sensitising in the absence of said candidate compound.

Thus, if a reduction or inhibition of the binding capacity is observed in the presence of said candidate compound, it can be concluded from this that said candidate compound is a compound able to decrease sensitisation.

Preferably, said candidate compound is able to be used on the skin and may be used in a cosmetic or dermatological composition.

Step a) can be carried out:

i) by prior contacting the compound identified as sensitising and the isolated polypeptide as previously defined, followed optionally by a first measurement of the binding of the compound identified as sensitising with said isolated polypeptide and then contacting with the candidate compound for decreasing sensitisation with the compound identified as sensitising bound to the isolated polypeptide;

ii) by prior contacting of the compound identified as sensitising and the candidate compound for decreasing sensitisation and then contacting the isolated polypeptide as previously defined with the compound identified as sensitising and the candidate compound for decreasing sensitisation; or iii) by simultaneously contacting the compound identified as sensitising, the candidate compound for decreasing sensitisation and the isolated polypeptide as previously defined.

Preferably, the isolated polypeptide comprises a sequence chosen from the sequences SEQ ID NO: 1, 2, 3, 4, 5, 6, 7, 8, 9, 10, 11, 12 and 13 and derivatives thereof.

The present invention also relates to a kit for implementing a method for the in vitro assessment of the sensitising potential of a test compound according to the present invention, comprising at least one isolated polypeptide comprising a sequence chosen from the sequences SEQ ID NO: 1, 2, 3, 4, 5, 6, 7, 8, 9, 10, 11, 12, 13, 14, 15, 16 and 17 and derivatives thereof.

Preferably, said isolated polypeptide comprises a sequence chosen from the sequences SEQ ID NO: 1, 2, 3, 4, 5, 6, 7, 8, 9, 10, 11, 12 and 13 and derivatives thereof, preferably from the sequences SEQ ID NO: 1, 2, 3, 4, and even more preferably from the sequences SEQ ID NO: 1 and SEQ ID NO: 3.

According to another aspect, the present invention also relates to a kit for implementing a method for selecting compounds able to decrease sensitisation according to the present invention, said kit comprising at least one polypeptide comprising a sequence chosen from the sequences SEQ ID NO: 1, 2, 3, 4, 5, 6, 7, 8, 9, 10, 11, 12, 13, 14, 15, 16 and 17 and derivatives thereof, and at least one compound identified as sensitising.

Preferably, the compound identified as sensitising is chosen from diphenylcyclopropenone, lauryl gallate, 3-3-dimethylaminopropylamine, cinnamic aldehyde, citral, 1,4-hydroquinone, glutaraldehyde, 1,2-benzisothiazolin-3-one, phenylacetaldehyde and lilial, preferentially from diphenylcyclopropenone, lauryl gallate, 1,4-hydroquinone and glutaraldehyde, and particularly preferably is diphenycyclopropenone.

Preferably, said isolated polypeptide comprises a sequence chosen from the sequences SEQ ID NO: 1, 2, 3, 4, 5, 6, 7, 8, 9, 10, 11, 12 and 13 and derivatives thereof, preferentially from the sequences SEQ ID NO: 1, 2, 3, 4, and even more preferably from the sequences SEQ ID NO: 1 and SEQ ID NO: 3.

According to another aspect, the present invention relates to the use of a polypeptide comprising a sequence chosen from the sequences SEQ ID NO: 1, 2, 3, 4, 5, 6, 7, 8, 9, 10, 11, 12, 13, 14, 15, 16 and 17 and derivatives thereof, for the in vitro assessment of the sensitising potential of a test compound.

Preferably, said isolated polypeptide comprises a sequence chosen from the sequences SEQ ID NO: 1, 2, 3, 4, 5, 6, 7, 8, 9, 10, 11, 12 and 13 and derivatives thereof, preferentially from the sequences SEQ ID NO: 1, 2, 3, 4, and even more preferentially from the sequences SEQ ID NO: 1 and SEQ ID NO: 3.

EXAMPLES

Example 1

A test with 0.5 mM of polypeptide and 5 mM of test compound is carried out under the following conditions:

The reaction mixture containing 40 µl of peptide solution (1.25 mM stock solution in a 100 mM ammonium acetate buffer at pH 10.2 and the polypeptide of sequence SEQ ID NO: 18, SEQ ID NO: 7 in which X1, X2, X3 and X4 each represents a lysine, or SEQ ID NO: 8 in which X1, X2, X3 and X4 each represents a lysine), 35 µl of 100 mM ammonium acetate buffer solution, at pH 10.2, 20 µl of acetonitrile and 5 µl of solution to be tested (100 mM stock solution in acetonitrile or a 50% acetonitrile 50% DMSO mixture) was prepared and then stirred.

The sequence SEQ ID NO: 18, which is not a lipocalin derivative, was used as a positive control. This sequence corresponds to the following sequence:

Ac-RFAAKAA-NH$_2$ (SEQ ID NO: 18)

The reaction mixture was then put to incubate at 30° C. for 4 hours and in darkness.

HPLC analysis was then carried out at a gradient of 10% to 45% of buffer B (acetonitrile+0.08% of trifluoroacetic acid (TFA)) in 20 minutes (buffer A: water+0.1% of TFA), rate 1 ml/minute. Detection was carried out under UV at 230 nm.

The control without allergen consisted of 40 µl of buffer solution.

The synthesis reagents (Fmoc amino acids, synthesis resin) were obtained from IRIS BIOTECH (Germany), the organic solvents were obtained from SDS/CARLO ERBA (France) and the acetonitrile was obtained from FISHER BIOBLOCK (France).

The results are presented in table 1.

TABLE 1

| % fixing | SEQ ID NO: 18 | SEQ ID NO: 7, wherein X1, X2, X3 and X4 each represent a lysine | SEQ ID NO: 8, where in X1, X2, X3 and X4 each represent a lysine |
|---|---|---|---|
| LG (lauryl gallate) | 62% | 100% | 63% |
| CA (cinnamic aldehyde) | 17% | 100% | 30% |
| Cbz (negative control) | 0% | 0% | 0% |

Similar results were observed when, in the sequence SEQ ID NO: 7 and in the sequence SEQ ID NO: 8, X1, X2, X3 and X4 are independently chosen from lysine, ornithine, diaminobutyrate or diaminopropionate, and at least one from X1, X2, X3 and X4 is not lysine.

A high of percentage fixing of lauryl gallate is observed, which has a strong sensitising capacity for the 3 sequences studied, a high fixing percentage of cinnamic aldehyde, which has a moderate sensitising capacity for the sequence SEQ ID NO: 7 and moderate for the sequences SEQ ID NO: 8 and SEQ ID NO: 18.

Example 2

A test with 0.5 mM of polypeptide of sequence SEQ ID NO: 29 and 5 mM of test compound was carried in accordance with the same protocol as that described for example 1.

The sequence SEQ ID NO: 19, which is not a lipocalin derivative, was used as a positive control. This sequence corresponds to the following sequence:

Ac-RFAACAA-NH$_2$ (SEQ ID NO: 19)

The buffer used was 100 mM TRIS-HCl at pH 8.3.

TABLE 2

| % fixing | SEQ ID NO: 19 |
|---|---|
| DPCP | 96% |
| LG | 100% |
| 3-DMAPA | 25% |
| CA | n/a |
| Cal | 70% |
| Cbz (negative control) | 0% |

Example 3

A test with twice 0.5 mM of polypeptide of sequence SEQ ID NO: 19 and SEQ ID NO: 8, wherein X1, X2, X3 and X4 each represent a lysine, and 5 mM of test compound, was carried out in accordance with the same protocol as that described for example 1.

The buffer used was 100 Mm TRIS-HCl at pH 8.3, pH 9.2 and pH 8.8.

The results are presented in table 3.

TABLE 3

| | pH 8.3 | | pH 9.2 | | pH 8.8 | |
|---|---|---|---|---|---|---|
| | SEQ ID NO: 19 | SEQ ID NO: 8, wherein X1, X2, X3 and X4 each represents a lysine | SEQ ID NO: 19 | SEQ ID NO: 8, wherein X1, X2, X3 and X4 each represents a lysine | SEQ ID NO: 19 | SEQ ID NO: 8, wherein X1, X2, X3 and X4 each represents a lysine |
| HQ | 100% | 100% | n/a | Fixing | n/a | 100% |
| GA | 22% | 50% | 33% | 50% | Fixing | 100% |
| Ben | Fixing | 100% | n/a | 0% | Fixing | 100% |
| PA | 100% | Fixing | 86% | 21% | n/a | 0% |
| Li | 36% | 0% | 0% | n/a | n/a | n/a |
| LA (negative control) | 0% | 0% | 0% | 0% | 0% | 0% |

The term "fixing" indicates that a fixing exists, but that this is not quantifiable.
n/a: fixing cannot be determined at an identical retention time.

It is observed that better results are obtained at a pH of 8.3.

Similar results were observed when, in the sequence SEQ ID NO: 8, X1, X2, X3 and X4 are independently chosen from lysine, ornithine, diaminobutyrate or diaminoproprionate, and at least one from X1, X2, X3 and X4 is not lysine.

Example 4

A test with twice 0.5 mM of polypeptide of sequence SEQ ID NO: 19 and SEQ ID NO: 8, wherein X1, X2, X3 and X4 each represent a lysine, and 5 mM of test compound, was carried in accordance with the same protocol as that described for example 1.

The buffer used was TRIS-HCl at 100 mM.

The results are presented in table 4.

TABLE 4

| % fixing (mean) | SEQ ID NO: 19 | SEQ ID NO: 8, in which X1, X2, X3 and X4 each represent a lysine |
|---|---|---|
| HQ | 90% | 100% |
| GA | 33% | 50% |
| Ben | 90% | n/a |
| PA | 81% | Fixing |
| Li | 18% | 0% |
| LA (negative control) | 0% | 0% |
| DPCP | 100% | n/a |
| LG | 100% | 62% |
| DMAPA | 15% | 6% |
| CA | n/a | 30% |
| Cal | 46% | 70% |
| Cbz (negative control) | 0% | 0% |

Similar results were observed when, in the sequence SEQ ID NO: 8, X1, X2, X3 and X4 are independently chosen from lysine, ornithine, diaminobutyrate or diaminoproprionate, and at least one from X1, X2, X3 and X4 is not lysine.

Example 5

A test with twice 0.5 mM of polypeptides of sequences SEQ ID NO: 19 and SEQ ID NO: 1 wherein X1, X2, X3 and X4 each represent a lysine, and having an NH2 group at its C-Terminal end, and SEQ ID NO: 8 wherein X1, X2, X3 and X4 each represent a lysine, and 5 mM of test compound, was carried out in accordance with the same protocol as that described for example 1.

The buffer used was TRIS-HCl at 100 mM.

The results are presented in table 5.

TABLE 5

| % fixing | SEQ ID NO: 19 | SEQ ID NO: 8, wherein X1, X2, X3 and X4 each represent a lysine | SEQ ID NO: 1, wherein X1, X2, X3 and X4 each represent a lysine, and having a NH2 group at its C-Terminal end |
|---|---|---|---|
| HQ | 90% | 100% | 82.5% |
| GA | 33% | 50% | 83% |
| Ben | 90% | n/a | n/a |
| PA | 81% | Fixing | 54% |
| Li | 18% | 0% | 12% |
| LA (negative control) | 0% | 0% | 1% |
| DPCP | 100% | n/a | 83.5% |
| LG | 100% | 62% | 41.5% |
| DMAPA | 15% | 6% | 3% |
| CA | n/a | 30% | n/a |
| Cal | 46% | 70% | 64% |
| Cbz (negative control) | 0% | 0% | 7.5% |

Similar results were observed when, in the sequence SEQ ID NO: 1 or in the sequence SEQ ID NO: 8, X1, X2, X3 and X4 are independently chosen from lysine, ornithine, diaminobutyrate or diaminoproprionate, and at least one from X1, X2, X3 and X4 is not lysine.

It should be noted, in the case of the tests of SEQ ID NO: 1, the signal was disturbed, preventing measurements greater than 82-83% fixing. These values consequently represent a minimum.

During a series of measurements carried out with the sequence SEQ ID NO: 1, the lauryl gallate and phenylacetyldehyde very greatly precipitated, thus explaining the medium results obtained.

A coelution of the polypeptide with the allergens cinnamic aldehyde and 1,2-Benzisothiazolin-3-one was observed.

The results show that the polypeptide of sequence SEQ ID NO: 1 makes it possible to obtain results similar to the use of the 2 polypeptides of sequence SEQ ID NO: 19 and SEQ ID NO: 8, while having the following advantages:
- short peptide, 11 residues, synthesis and purification without difficulties
- weak dimerisation
- excellent solubility, easy to manipulate (slightly electrostatic)
- unique test and conditions
- makes it possible to detect both allergens fixed by cysteine and those fixed by lysine.

The invention claimed is:

1. A method for the in vitro assessment of the skin sensitising potential of a test compound, comprising the steps of:
   a) contacting a test compound with an isolated polypeptide comprising a sequence selected from the group consisting of the sequences SEQ ID NOS: 1, 2, 3 and 4 and derivatives thereof;
   b) measuring any binding of said test compound with said polypeptide
   wherein the derivatives thereof are isolated polypeptides comprising one or more conservative sequence mutations, wherein the conservative sequence mutations do not alter pKa values of cysteine thiol groups and/or lysine residues, wherein the conservative sequence mutations do not modify activity of the isolated polypeptide, and
   wherein each of the derivatives thereof has at least 95% sequence identity with one of the group consisting of the sequences SEQ ID NOS: 1, 2, 3 and 4.

2. The method according to claim 1, wherein said test compound is able to be applied on the skin.

3. The method according to claim 1, wherein said test compound is able to form part of the composition of a dermatological or cosmetic composition.

4. An in vitro method for selecting a compound able to decrease skin sensitisation, comprising the steps of:
   a) contacting a compound identified as sensitising, an isolated polypeptide comprising a sequence chosen in the group consisting of the sequences SEQ ID NOS: 1, 2, 3 and 4 and derivatives thereof, and a candidate compound for decreasing skin sensitisation;
   b) measuring any binding of the compound indentified as sensitising with said polypeptide,
   wherein the derivatives thereof are isolated polypeptides comprising one or more conservative sequence mutations, wherein the conservative sequence mutations do not alter pKa values of cysteine thiol groups and/or lysine residues, wherein the conservative sequence mutations do not modify activity of the isolated polypeptide, and
   wherein each of the derivatives thereof has at least 95% sequence identity with one of the group consisting of the sequences SEQ ID NOS: 1, 2, 3 and 4.

5. The method according to claim 4, wherein the compound identified as skin sensitising is selected from the group consisting of diphenylcyclopropenone, lauryl gallate, 3-3-dimethylaminopropylamine, cinnamic aldehyde, citral, 1,4-hydroquinone, glutaraldehyde, 1,2-benzisothiazolin-3-one, phenylacetaldehyde and lilial.

6. An isolated polypeptide comprising a sequence selected from the group consisting of SEQ ID NOS: 1, 2, 3 and 4.

7. The isolated polypeptide according to claim 6, wherein said sequence SEQ ID NOS: 1, 2, 3 and 4 further comprises an acetyl group at its N-Terminal end.

8. An isolated polypeptide according to claim 6 or 7, wherein said sequence SEQ ID NOS: 1, 2, 3 and 4 further comprises an amine or amide group at its C-Terminal end.

9. A synthetic nucleic acid comprising a sequence encoding the isolated polypeptide according to claim 6.

10. A kit comprising at least one isolated polypeptide comprising a sequence selected from the group consisting of SEQ ID NO: 1, 2, 3 and 4 and derivatives thereof, wherein the derivatives thereof are isolated polypeptides comprising one or more conservative sequence mutations, wherein the conservative sequence mutations do not alter pKa values of cysteine thiol groups and/or lysine residues, wherein the conservative sequence mutations do not modify activity of the isolated polypeptide, and wherein each of the derivatives thereof has at least 95% sequence identity with one of the group consisting of the sequences SEQ ID NO: 1, 2, 3 and 4.

11. The method according to claim 1, wherein contacting the test compound with an isolated polypeptide comprises contacting the test compound with an isolated polypeptide selected from the group consisting of the sequences SEQ ID NO: 1, 2, 3 and 4.

12. The method according to claim 4, wherein contacting the test compound with an isolated polypeptide comprises contacting the test compound with an isolated polypeptide selected from the group consisting of the sequences SEQ ID NO: 1, 2, 3 and 4.

13. The kit according to claim 11, comprising at least one isolated polypeptide comprising a sequence selected from the group consisting of SEQ ID NO: 1, 2, 3 and 4

* * * * *

SEQUENCE LISTING

<160> NUMBER OF SEQ ID NOS: 32

<210> SEQ ID NO 1
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is lysine, ornithin, diaminobutyrate or
      diaminopropionate
<220> FEATURE:
<221> NAME/KEY: misc_feature
<222> LOCATION: (5)..(5)
<223> OTHER INFORMATION: Xaa is lysine, ornithin, diaminobutyrate or
      diaminopropionate
<220> FEATURE:
<221> NAME/KEY: misc_feature
<222> LOCATION: (9)..(9)
<223> OTHER INFORMATION: Xaa is lysine, ornithin, diaminobutyrate or
      diaminopropionate
<220> FEATURE:
<221> NAME/KEY: misc_feature
<222> LOCATION: (11)..(11)
<223> OTHER INFORMATION: Xaa is lysine, ornithin, diaminobutyrate or
      diaminopropionate

<400> SEQUENCE: 1

Xaa Ala Cys Ala Xaa Asp Glu Leu Xaa Glu Xaa
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is lysine, ornithin, diaminobutyrate or
      diaminopropionate
<220> FEATURE:
<221> NAME/KEY: misc_feature
<222> LOCATION: (3)..(3)
<223> OTHER INFORMATION: Xaa is lysine, ornithin, diaminobutyrate or
      diaminopropionate
<220> FEATURE:
<221> NAME/KEY: misc_feature
<222> LOCATION: (7)..(7)
<223> OTHER INFORMATION: Xaa is lysine, ornithin, diaminobutyrate or
      diaminopropionate
<220> FEATURE:
<221> NAME/KEY: misc_feature
<222> LOCATION: (11)..(11)
<223> OTHER INFORMATION: Xaa is lysine, ornithin, diaminobutyrate or
      diaminopropionate

<400> SEQUENCE: 2

Xaa Glu Xaa Leu Glu Asp Xaa Ala Cys Ala Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)

```
<223> OTHER INFORMATION: Xaa is lysine, ornithine,diaminobutyrate or
      diaminopropionate
<220> FEATURE:
<221> NAME/KEY: misc_feature
<222> LOCATION: (8)..(8)
<223> OTHER INFORMATION: Xaa is lysine, ornithine,diaminobutyrate or
      diaminopropionate
<220> FEATURE:
<221> NAME/KEY: misc_feature
<222> LOCATION: (10)..(10)
<223> OTHER INFORMATION: Xaa is lysine, ornithine,diaminobutyrate or
      diaminopropionate

<400> SEQUENCE: 3

Glu Cys Gly Xaa Asp Glu Leu Xaa Glu Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is lysine, ornithine, diaminobutyrate or
      diaminopropionate
<220> FEATURE:
<221> NAME/KEY: misc_feature
<222> LOCATION: (3)..(3)
<223> OTHER INFORMATION: Xaa is lysine, ornithine, diaminobutyrate or
      diaminopropionate
<220> FEATURE:
<221> NAME/KEY: misc_feature
<222> LOCATION: (7)..(7)
<223> OTHER INFORMATION: Xaa is lysine, ornithine, diaminobutyrate or
      diaminopropionate

<400> SEQUENCE: 4

Xaa Glu Xaa Leu Glu Asp Xaa Gly Cys Glu
1               5                   10

<210> SEQ ID NO 5
<211> LENGTH: 28
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa is lysine, ornithin, diaminobutyrate or
      diaminopropionate
<220> FEATURE:
<221> NAME/KEY: misc_feature
<222> LOCATION: (13)..(13)
<223> OTHER INFORMATION: Xaa is lysine, ornithin, diaminobutyrate or
      diaminopropionate
<220> FEATURE:
<221> NAME/KEY: misc_feature
<222> LOCATION: (21)..(21)
<223> OTHER INFORMATION: Xaa is lysine, ornithin, diaminobutyrate or
      diaminopropionate

<400> SEQUENCE: 5

Leu Tyr Gly Arg Thr Xaa Glu Leu Thr Ser Glu Leu Xaa Glu Asn Phe
1               5                   10                  15

Ile Arg Phe Ser Xaa Ser Leu Gly Leu Pro Glu Asn
            20                  25

<210> SEQ ID NO 6
<211> LENGTH: 28
<212> TYPE: PRT
<213> ORGANISM: Homo sapiens
```

```
<220> FEATURE:
<221> NAME/KEY: misc_feature
<222> LOCATION: (13)..(13)
<223> OTHER INFORMATION: Xaa is lysine, ornithin, diaminobutyrate or
      diaminopropionate
<220> FEATURE:
<221> NAME/KEY: misc_feature
<222> LOCATION: (21)..(21)
<223> OTHER INFORMATION: Xaa is lysine, ornithin, diaminobutyrate or
      diaminopropionate

<400> SEQUENCE: 6

Leu Tyr Ser Arg Ser Gln Asn Pro Arg Ala Glu Val Xaa Glu His Phe
1               5                   10                  15

Thr Thr Phe Ala Xaa Ser Leu Gly Phe Thr Glu Glu
            20                  25

<210> SEQ ID NO 7
<211> LENGTH: 25
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa is lysine, ornithin, diaminobutyrate or
      diaminopropionate
<220> FEATURE:
<221> NAME/KEY: misc_feature
<222> LOCATION: (13)..(13)
<223> OTHER INFORMATION: Xaa is lysine, ornithin, diaminobutyrate or
      diaminopropionate
<220> FEATURE:
<221> NAME/KEY: misc_feature
<222> LOCATION: (20)..(20)
<223> OTHER INFORMATION: Xaa is lysine, ornithin, diaminobutyrate or
      diaminopropionate
<220> FEATURE:
<221> NAME/KEY: misc_feature
<222> LOCATION: (25)..(25)
<223> OTHER INFORMATION: Xaa is lysine, ornithin, diaminobutyrate or
      diaminopropionate

<400> SEQUENCE: 7

Leu Tyr Gly Arg Thr Xaa Glu Leu Ser Pro Glu Leu Xaa Glu Arg Phe
1               5                   10                  15

Thr Phe Ala Xaa Ser Leu Gly Leu Xaa
            20                  25

<210> SEQ ID NO 8
<211> LENGTH: 26
<212> TYPE: PRT
<213> ORGANISM: Mus musculus
<220> FEATURE:
<221> NAME/KEY: misc_feature
<222> LOCATION: (9)..(9)
<223> OTHER INFORMATION: Xaa is lysine, ornithin, diaminobutyrate or
      diaminopropionate
<220> FEATURE:
<221> NAME/KEY: misc_feature
<222> LOCATION: (13)..(13)
<223> OTHER INFORMATION: Xaa is lysine, ornithin, diaminobutyrate or
      diaminopropionate
<220> FEATURE:
<221> NAME/KEY: misc_feature
<222> LOCATION: (15)..(15)
<223> OTHER INFORMATION: Xaa is lysine, ornithin, diaminobutyrate or
      diaminopropionate
<220> FEATURE:
<221> NAME/KEY: misc_feature
<222> LOCATION: (21)..(21)
<223> OTHER INFORMATION: Xaa is lysine, ornithin, diaminobutyrate or
      diaminopropionate

<400> SEQUENCE: 8
```

```
Leu Tyr Ser Arg Thr Gln Thr Leu Xaa Asp Glu Leu Xaa Glu Xaa Phe
1               5                   10                  15

Thr Thr Phe Ser Xaa Ala Gln Gly Leu Thr
                20                  25

<210> SEQ ID NO 9
<211> LENGTH: 8
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa is lysine, ornithin, diaminobutyrate or
      diaminopropionate

<400> SEQUENCE: 9

Arg Gln Asn Gln Cys Glu Thr Xaa
1               5

<210> SEQ ID NO 10
<211> LENGTH: 9
<212> TYPE: PRT
<213> ORGANISM: Homo sapiens
<220> FEATURE:
<221> NAME/KEY: misc_feature
<222> LOCATION: (7)..(7)
<223> OTHER INFORMATION: Xaa is lysine, ornithin, diaminobutyrate or
      diaminopropionate

<400> SEQUENCE: 10

Thr Leu Tyr Gly Arg Thr Xaa Glu Leu
1               5

<210> SEQ ID NO 11
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa is lysine, ornithin, diaminobutyrate or
      diaminopropionate
<220> FEATURE:
<221> NAME/KEY: misc_feature
<222> LOCATION: (9)..(9)
<223> OTHER INFORMATION: Xaa is lysine, ornithin, diaminobutyrate or
      diaminopropionate

<400> SEQUENCE: 11

Xaa Glu Arg Phe Thr Arg Phe Ala Xaa
1               5

<210> SEQ ID NO 12
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa is lysine, ornithin, diaminobutyrate or
      diaminopropionate
<220> FEATURE:
<221> NAME/KEY: misc_feature
<222> LOCATION: (3)..(3)
<223> OTHER INFORMATION: Xaa is lysine, ornithin, diaminobutyrate or
      diaminopropionate
<220> FEATURE:
<221> NAME/KEY: misc_feature
<222> LOCATION: (9)..(9)
<223> OTHER INFORMATION: Xaa is lysine, ornithin, diaminobutyrate or
      diaminopropionate
```

<400> SEQUENCE: 12

Xaa Glu Xaa Phe Thr Thr Phe Ser Xaa
1               5

<210> SEQ ID NO 13
<211> LENGTH: 9
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa is lysine, ornithin, diaminobutyrate or
      diaminopropionate

<400> SEQUENCE: 13

Leu Tyr Gly Arg Thr Xaa Glu Leu Ser
1               5

<210> SEQ ID NO 14
<211> LENGTH: 198
<212> TYPE: PRT
<213> ORGANISM: Homo sapiens

<400> SEQUENCE: 14

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
    130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Tyr Leu Gly Leu Pro Glu Asn His Ile Val Phe Pro Val Pro Ile
            180                 185                 190

Asp Gln Cys Ile Asp Gly
        195

<210> SEQ ID NO 15
<211> LENGTH: 200
<212> TYPE: PRT
<213> ORGANISM: Mus musculus

<400> SEQUENCE: 15

Met Ala Leu Ser Val Met Cys Leu Gly Leu Ala Leu Leu Gly Val Leu
1               5                   10                  15

```
Gln Ser Gln Ala Gln Asp Ser Thr Gln Asn Leu Ile Pro Ala Pro Ser
            20                  25                  30

Leu Leu Thr Val Pro Leu Gln Pro Asp Phe Arg Ser Asp Gln Phe Arg
        35                  40                  45

Gly Arg Trp Tyr Val Val Gly Leu Ala Gly Asn Ala Val Gln Lys Lys
50                  55                  60

Thr Glu Gly Ser Phe Thr Met Tyr Ser Thr Ile Tyr Glu Leu Gln Glu
65                  70                  75                  80

Asn Asn Ser Tyr Asn Val Thr Ser Ile Leu Val Arg Asp Gln Asp Gln
                85                  90                  95

Gly Cys Arg Tyr Trp Ile Arg Thr Phe Val Pro Ser Ser Arg Ala Gly
            100                 105                 110

Gln Phe Thr Leu Gly Asn Met His Arg Tyr Pro Gln Val Gln Ser Tyr
        115                 120                 125

Asn Val Gln Val Ala Thr Thr Asp Tyr Asn Gln Phe Ala Met Val Phe
    130                 135                 140

Phe Arg Lys Thr Ser Glu Asn Lys Gln Tyr Phe Lys Ile Thr Leu Tyr
145                 150                 155                 160

Gly Arg Thr Lys Glu Leu Ser Pro Glu Leu Lys Glu Arg Phe Thr Arg
                165                 170                 175

Phe Ala Lys Ser Leu Gly Leu Lys Asp Asp Asn Ile Ile Phe Ser Val
            180                 185                 190

Pro Thr Asp Gln Cys Ile Asp Asn
            195                 200

<210> SEQ ID NO 16
<211> LENGTH: 190
<212> TYPE: PRT
<213> ORGANISM: Homo sapiens

<400> SEQUENCE: 16

Met Ala Thr His His Thr Leu Trp Met Gly Leu Ala Leu Leu Gly Val
1               5                   10                  15

Leu Gly Asp Leu Gln Ala Ala Pro Glu Ala Gln Val Ser Val Gln Pro
            20                  25                  30

Asn Phe Gln Gln Asp Lys Phe Leu Gly Arg Trp Phe Ser Ala Gly Leu
        35                  40                  45

Ala Ser Asn Ser Ser Trp Leu Arg Glu Lys Lys Ala Ala Leu Ser Met
50                  55                  60

Cys Lys Ser Val Val Ala Pro Ala Thr Asp Gly Gly Leu Asn Leu Thr
65                  70                  75                  80

Ser Thr Phe Leu Arg Lys Asn Gln Cys Glu Thr Arg Thr Met Leu Leu
                85                  90                  95

Gln Pro Ala Gly Ser Leu Gly Ser Tyr Ser Tyr Arg Ser Pro His Trp
            100                 105                 110

Gly Ser Thr Tyr Ser Val Ser Val Val Glu Thr Asp Tyr Asp Gln Tyr
        115                 120                 125

Ala Leu Leu Tyr Ser Gln Gly Ser Lys Gly Pro Gly Glu Asp Phe Arg
    130                 135                 140

Met Ala Thr Leu Tyr Ser Arg Thr Gln Thr Pro Arg Ala Glu Leu Lys
145                 150                 155                 160

Glu Lys Phe Thr Ala Phe Cys Lys Ala Gln Gly Phe Thr Glu Asp Thr
                165                 170                 175

Ile Val Phe Leu Pro Gln Thr Asp Lys Cys Met Thr Glu Gln
            180                 185                 190
```

```
<210> SEQ ID NO 17
<211> LENGTH: 189
<212> TYPE: PRT
<213> ORGANISM: Mus musculus

<400> SEQUENCE: 17

Met Ala Ala Leu Arg Met Leu Trp Met Gly Leu Val Leu Leu Gly Leu
1               5                   10                  15

Leu Gly Phe Pro Gln Thr Pro Ala Gln Gly His Asp Thr Val Gln Pro
            20                  25                  30

Asn Phe Gln Gln Asp Lys Phe Leu Gly Arg Trp Tyr Ser Ala Gly Leu
        35                  40                  45

Ala Ser Asn Ser Ser Trp Phe Arg Glu Lys Lys Ala Val Leu Tyr Met
    50                  55                  60

Cys Lys Thr Val Val Ala Pro Ser Thr Glu Gly Gly Leu Asn Leu Thr
65                  70                  75                  80

Ser Thr Phe Leu Arg Lys Asn Gln Cys Glu Thr Lys Ile Met Val Leu
                85                  90                  95

Gln Pro Ala Gly Ala Pro Gly His Tyr Thr Tyr Ser Ser Pro His Ser
            100                 105                 110

Gly Ser Ile His Ser Val Ser Val Val Glu Ala Asn Tyr Asp Glu Tyr
        115                 120                 125

Ala Leu Leu Phe Ser Arg Gly Thr Lys Gly Pro Gly Gln Asp Phe Arg
    130                 135                 140

Met Ala Thr Leu Tyr Ser Arg Thr Gln Thr Leu Lys Asp Glu Leu Lys
145                 150                 155                 160

Glu Lys Phe Thr Thr Phe Ser Lys Ala Gln Gly Leu Thr Glu Glu Asp
                165                 170                 175

Ile Val Phe Leu Pro Gln Pro Asp Lys Cys Ile Gln Glu
            180                 185

<210> SEQ ID NO 18
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: AMIDATION

<400> SEQUENCE: 18

Arg Phe Ala Ala Lys Ala Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: AMIDATION
```

```
<400> SEQUENCE: 19

Arg Phe Ala Ala Cys Ala Ala
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Lys Ala Cys Ala Lys Asp Glu Leu Lys Glu Lys
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic

<400> SEQUENCE: 21

Lys Glu Lys Leu Glu Asp Lys Ala Cys Ala Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Glu Cys Gly Lys Asp Glu Leu Lys Glu Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Lys Glu Lys Leu Glu Asp Lys Gly Cys Glu
1               5                   10

<210> SEQ ID NO 24
<211> LENGTH: 28
<212> TYPE: PRT
<213> ORGANISM: Artificial Sequence
<220> FEATURE:
<223> OTHER INFORMATION: Synthetic

<400> SEQUENCE: 24

Leu Tyr Gly Arg Thr Lys Glu Leu Thr Ser Glu Leu Lys Glu Asn Phe
1               5                   10                  15

Ile Arg Phe Ser Lys Ser Leu Gly Leu Pro Glu Asn
            20                  25

<210> SEQ ID NO 25
<211> LENGTH: 28
<212> TYPE: PRT
<213> ORGANISM: Artificial Sequence
<220> FEATURE:
```

<223> OTHER INFORMATION: Synthetic

<400> SEQUENCE: 25

Leu Tyr Ser Arg Ser Gln Asn Pro Arg Ala Glu Val Lys Glu His Phe
1               5                   10                  15

Thr Thr Phe Ala Lys Ser Leu Gly Phe Thr Glu Glu
            20                  25

<210> SEQ ID NO 26
<211> LENGTH: 25
<212> TYPE: PRT
<213> ORGANISM: Artificial Sequence
<220> FEATURE:
<223> OTHER INFORMATION: Synthetic

<400> SEQUENCE: 26

Leu Tyr Gly Arg Thr Lys Glu Leu Ser Pro Glu Leu Lys Glu Arg Phe
1               5                   10                  15

Thr Phe Ala Lys Ser Leu Gly Leu Lys
            20                  25

<210> SEQ ID NO 27
<211> LENGTH: 26
<212> TYPE: PRT
<213> ORGANISM: Artificial Sequence
<220> FEATURE:
<223> OTHER INFORMATION: Synthetic

<400> SEQUENCE: 27

Leu Tyr Ser Arg Thr Gln Thr Leu Lys Asp Glu Leu Lys Glu Lys Phe
1               5                   10                  15

Thr Thr Phe Ser Lys Ala Gln Gly Leu Thr
            20                  25

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Arg Gln Asn Gln Cys Glu Thr Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Thr Leu Tyr Gly Arg Thr Lys Glu Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Lys Glu Arg Phe Thr Arg Phe Ala Lys
1               5

```
<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Lys Glu Lys Phe Thr Thr Phe Ser Lys
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Leu Tyr Gly Arg Thr Lys Glu Leu Ser
1               5
```